United States Patent [19]

Mest

[11] Patent Number: 5,977,121
[45] Date of Patent: *Nov. 2, 1999

[54] USE OF MOXONIDINE FOR THE TREATMENT OF ATHEROSCLEROSIS

[75] Inventor: Hans Jürgen Mest, Quickborn, Germany

[73] Assignee: Eli Lilly and Company, Indianapolis, Ind.

[*] Notice: This patent issued on a continued prosecution application filed under 37 CFR 1.53(d), and is subject to the twenty year patent term provisions of 35 U.S.C. 154(a)(2).

[21] Appl. No.: 08/913,063

[22] PCT Filed: Feb. 21, 1996

[86] PCT No.: PCT/EP96/00783

§ 371 Date: Dec. 22, 1997

§ 102(e) Date: Dec. 22, 1997

[87] PCT Pub. No.: WO96/26728

PCT Pub. Date: Sep. 6, 1996

[30]   Foreign Application Priority Data

Feb. 28, 1995  [EP]  European Pat. Off. .............. 95301295

[51] Int. Cl.$^6$ .......................... A61K 31/415; A01N 43/50
[52] U.S. Cl. .............................................................. 514/269
[58] Field of Search .............................................. 514/269

[56]   References Cited

U.S. PATENT DOCUMENTS

| | | | |
|---|---|---|---|
| 4,323,570 | 4/1982 | Stenzel et al. ........................... | 424/251 |
| 4,778,678 | 10/1988 | Guse et al. ............................... | 424/487 |
| 4,882,163 | 11/1989 | Guse et al. ............................... | 424/448 |
| 4,952,410 | 8/1990 | Armah et al. ........................... | 424/465 |
| 5,574,059 | 11/1996 | Regunathan et al. .................... | 514/397 |
| 5,707,798 | 1/1998 | Brann ......................................... | 435/6 |
| 5,712,283 | 1/1998 | Kaan et al. ............................... | 514/269 |
| 5,732,717 | 3/1998 | Watanabe et al. ....................... | 128/898 |

FOREIGN PATENT DOCUMENTS

| | | |
|---|---|---|
| 0689837 A2 | 1/1996 | European Pat. Off. . |
| 3904795 | 8/1990 | Germany . |
| Wo 95/03798 | 2/1995 | WIPO . |

OTHER PUBLICATIONS

T. Irzyniec, et al., "Beneficial Effect of Nifedipine and Moxonidine on Glomerulosclerosis in Spontaneously Hypertensive Rats: A Micromorphometric Study" *AJH*, vol. 5, No. 7, pp. 437–443, (1992).
H. Rupp, "Reaching the Goal by Regulation of the Sympathetic System; Antihypertensive Agents in Case of Hyperinsulinemia", *Therapiewoche*, vol. 43. No. 32/33, pp. 1686–1693, (1993). (with English translation).
W. Motz et al., Benefits and Risks of Antihypertensive Therapy from the Cardiologic Point of View, *Zeitschrift fur Kardiologie 83*, pp. 179–187 (1994). (with English translation).
B.E. Strauer, "Combatting Hypertrophy and Microangiopathy [Hypertrophie und mikroangiopathie bekampfen]", *Therapiewoche Schweiz*, vol. 10, No. 1, pp. 40–43, (1994). (with English translation).
H. Rupp, "Mechanisms of Cardiac Cell Damage Due to Catecholamines: Significance of Drugs Regulating Central Sympathetic Outflow," *J. of Cardiovascular Pharma.* vol. 24, No. 1, pp. S16–S24, (1994).
Ollivier et al J. Cardiovas. Pharmacol. 24(Suppl. 1) S39–S48 (1994).
Rupp et al Can. Mol. Cell. Biochem. 132(1): 69–80 (1994).
Palatini et al Jl. Human Hypertension 11/Suppl. 1 (S19–S27) (1993).
Ernsberger et al Cardiovascular Drugs & Therapy 10/Suppl. 1: 275–282 (1996).
Scientific Information Brochure, "Selective imidazoline receptor agonist for the treatment of hypertension," Beiersdorf–Lilly and Lilly Deutshland (no date).
J.P. Ollivier, et al., "$I_1$–Imidazoline–Receptor Agonists in the Treatment of Hypertension: An Appraisal of Clinical Experience," *Journal of Cardiovascular Pharmacology*, 24 (Suppl. 1), S39–S48 (1994).
P. Ernsberger, et al., "Moxonodine: A Second–Generation Central Antihypertensive Agent", *Cardiovascular Drug Reviews*, vol. 11, No. 4, pp. 411–431, (1993).
M. Michel et al., "From $\alpha_2$–Adrenoceptors to Imidazoline Receptors: Putative Progress for Cardiovascular Therapy", *Journal of Cardiovascular Pharmacology*, 20 (Suppl. 4), S24–S30 (1992).
M.L. Mangiapane, et al., "Hemodynamic Effects of Moxonidine in the Rat", *The FASEB Journal*, vol. 9, No. 3, (1995).
H. Klepzig, Jr. et al., "Akuter und chronischer Einfluβ von Moxonidin auf Blutdruck und linksventrikulare Funktion in Ruhe und unter Belastung", *Herz/Kreislauf*, p. 2, (1990).
D. Knight, et al., "Effects of Moxonidine on the Development of Pacing–Induced Heart Failure in Conscious Dogs", *The FASEB Journal*, vol. 10, No. 3 (1996).
W. Motz, et al., "Antisympathonic Treatment. A New Way to Treat Heart Failure?", *The Journal of Heart Failure*, vol. 3, No. 1 (May 1996).
G. Treib, M.D., et al., "Long–term evaluation of the antihypertensive efficacy and tolerability of the orally acting imidazoline I1 receptor against moxonidine", *European Journal of Clinical Research*, vol. 7, pp. 227–240 (1995).
"Selective Imidazoline Receptor Agonist", *Moxonidine Physiotens*, (Jun., 1996).

(List continued on next page.)

*Primary Examiner*—Shep K. Rose
*Attorney, Agent, or Firm*—Brinks Hofer Gilson & Lione

[57]   ABSTRACT

There is disclosed a method of treating atherosclerosis, of preventing atherosclerotic lesions and plaque formation, of inhibiting atherogenesis, and of decreasing intracellular cholesterol accumulation through the administration of an effective amount of moxonodine, or a pharmaceutically acceptable salt thereof.

12 Claims, No Drawings

OTHER PUBLICATIONS

V. Mitrovic et al., emodynamic and Neurohumoral Effects of Alpha$_2$–Agonists–Moxonidine in Patients with Dilated Cardiomyopathy, *Rev. Eur. Biotech Med.*, vol. 12, 159 (1990).

Kirch et al., "Pharmacodynamic Action and Pharmacokinetics of Moxonidine After Single Oral Admininstration in Hypertensive Patients", *J. Clin. Pharmacol.* vol. 30, pp. 1088–1095 (1990).

Trenk, et al., "Pharmacokinetics of Moxonidine After Single and Repeated Daily Doses in Healthy Volunteers", vol. 27, pp. 988–993 (1987).

Kirch, et al., "The Influence of Renal Function on Clinical Pharmacokinetics of Moxonidine", *Clinical Pharmacokinetics*, 15, pp. 245–253 (1988).

Theodor, et al., "Absolute bioavailability of moxonidine", *European Journal of Drug Metabolism and Pharmacokinetics*, vol. 16, No. 2, pp. 153–159 (1991).

Theodor, et al., "Influence of food on the oral bioavailability of moxonidine", *European Journal of Drug Metabolism and Pharmacokinetics*, vol. 17, No. 1, pp. 61–66 (1992).

USE OF MOXONIDINE FOR THE TREATMENT OF ATHEROSCLEROSIS

CROSS REFERENCE

This application was filed under 35 U.S.C. §371 from the International Application No. PCT/EP96/00783 filed on Feb. 21, 1996, which International Application claims priority to European Patent Application No. EPO 95301295 filed Feb. 28, 1995.

This invention relates to the use of moxonidine in the treatment of atherosclerosis.

Moxonidine is a well known compound described in, for example, U.S. Pat. No. 4,323,570, for its properties as an agent for lowering blood pressure. The compound has the chemical formula 4-chloro-6-methoxy-2-methyl-5-(2-imidazolin-2-yl)aminopyrimidine.

Atherosclerosis is a major cause of death from ischaemia (ischaemic heart disease) in industrialised countries. It is now accepted that atherosclerosis begins with local injury to the arterial endothelium which results in proliferation of arterial smooth muscle cells with deposition of lipid and accumulation of macrophages. As the atherosclerotic plaque develops it progressively obstructs more and more of the blood vessel and can thus lead to ischaemia or infarction.

It has now been found that moxonidine is useful in the treatment of atherosclerosis.

Thus the invention comprises the use of moxonidine, or a pharmaceutically-acceptable acid addition salt thereof, in the treatment of atherosclerosis. More particularly, the invention comprises the use of moxonidine, or a pharmaceutically-acceptable acid addition salt thereof, in the preparation of a medicament for treating atherosclerosis.

It has been found in test models that moxonidine significantly decreases cholesterol accumulation induced by atherogenic serum, and also that it inhibits proliferation in cells cultured from an atherosclerotic plaque.

As mentioned above, moxonidine is the compound 4-chloro-6-methoxy-2-methyl-5(2-imidazolin-2-yl) aminopyrimidine, and can also be utilised in pharmaceutically-acceptable acid addition salt form. Suitable acid addition salts are the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicyclic, o-acetoxybenzoic, or organic sulphonic, 2-hydroxyethane sulphonic, toluene-p-sulphonic, or naphthalene-2-sulphonic acid.

The identification of those patients who are in need of treatment for atherosclerosis is well within the ability and knowledge of one skilled in the art. For example, individuals who are either suffering from clinically significant atherosclerosis or who are at risk of developing clinically significnat atheroslcerosis are patients in need of treatment for atherosclerosis. A clinician skilled in the art can readily determine, by the use of clinical tests, physical examination and medical/family history, if an individual is a patient in need of treatment for atherosclerosis.

An effective antiatherosclerotic amount of a compound of formula (1) is an amount which is effective in inhibiting development or growth of atherosclerosis in a patient in need thereof. As such, successful treatment of a patient for atherosclerosis is understood to include effectively slowing, interrupting, arresting, or stopping atherosclerotic lesion or plaque development or growth and does not necessarily indicate a total elimination of the atherosclerosis. It is further understood and appreciated by those skilled in the art that successful treatment for atherosclerosis can include prophylaxis in preventing atherosclerotic lesion or plaque formation, and inhibition of atherogenesis.

For the purpose of the invention, moxonidine may be administered by various routes, for example by the oral or rectal route, topically or parenterally, for example by injection or infusion, being usually employed in the form of a pharmaceutical composition. Such compositions are prepared in a manner well known in the pharmaceutical art. In making the composition the active ingredient will usually be mixed with a carrier, or diluted by a carrier, and/or enclosed within a carrier which may, for example, be in the form of a capsule, sachet, paper or other container. When the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, aerosols (as a solid or in a liquid medium), ointments containing for example up to 10% by weight of the active compound, soft and hard gelatin capsules, suppositories, injection solutions, suspensions, sterile packaged powders and as a topical patch. The preferred formulations are for oral dosage and are especially in table or capsule form.

Some examples of suitable carriers are lactose, dextrose, sucrose, sorbitol, mannitol, starches, ethylcellulose, gum acacia, calcium phosphate, alginates, tragacanth, gelatin, syrup, methyl cellulose, methyl- and propyl-hydroxybenzoate, talc magnesium stearate and mineral oil. The compositions of the injection may, as is well known in the art, be formulated so as to provide quick, sustained or delayed release of the active ingredient after administration to the patient.

Where the composition is formulated in unit dosage form, it is preferred that each unit dosage form contains from 0.01 mg to 2.0 mg, for example, from 0.05 mg to 1.0 mg. The term 'unit dosage form' refers to physically discrete units suitable as unit dosages for human subjects and animals, each unit containing a predetermined quantity of active material calculated to produce the desired therapeutic effect, in association with the required pharmaceutical carrier.

The active compound is effective over a wide dosage range and, for example, dosages per day will normally fall within the range of from 0.01 to 2.0 mg, more usually in the range of from 0.1 to 1.0 mg. Usually one dose a day, preferably in the morning, is sufficient. However, it will be understood that the amount administered will be determined by the physician in the light of the relevant circumstances including the condition to be treated and the chosen route of administration, and therefore the above dosage ranges are not intended to limit the scope of the invention in any way.

The following Example illustrates the activity of moxonidine in human cell tissue models.

EXAMPLE

The antiatherosclerotic and antiatherogenic effects of moxonidine were demonstrated in the following manner.

MATERIALS

Cell Culture

Subendothelial cells were isolated from grossly normal (atherosclerosis free) intima or atherosclerotic plaque of fresh autopsy-derived human aorta taken within 1–3 hours after sudden death. The procedures for the isolation and cultivation of human aortic cells are described in Orekhov et al., 1986, (Primary culture of human aortic intima cells as a model for testing antiatherosclerotic drugs. Effects of cyclic AMP, prostaglandins, calcium antagonists, antioxidants, and lipid-lowering agents. Atherosclerosis 60: 101–110).

METHODS

Antiatherosclerotic Effects

Moxonidine dissolved in 10 µl of Medium 199 was added to nine wells of a seven-day cell culture derived from atherosclerotic plaque. Simultaneously, 10 µl of Medium 199 containing 1 µCi/ml [$^3$H]thymidine (21 Ci/mmol, Amersham International, Amersham, U.K.) was added to three of the nine wells. To three other wells, 10 µl Medium 199 containing 1 µCi/ml [$^{14}$C]leucine (135 Ci/mmol, Amersham) was added. The remaining three wells were supplemented with 10 µl Medium 199. After a 24-hour incubation (on the eighth day in culture), total intracellular cholesterol content and DNA synthesis were determined. Total intracellular cholesterol was estimated in three wells free of radioactive precursors. Intracellular lipids were extracted with hexane-isopropanol mixture (3:2, v/v) [Hara A., Radin N. S., 1978, Lipid extraction of tissue with low-toxicity solvent, Anal. Biochem. 90: 420–426]. The total cholesterol content in the lipid extracts was determined as described [Orekhov et al., 1986] using Boehringer Mannheim Monotest$^R$, Cholesterol CHOD-PAP Method (Boehringer Mannheim GmbH, Mannheim, Germany). DNA synthesis was evaluated by the incorporation of [$^3$H]thymidine into acid-insoluble cell fraction as described in Orekhov et al., 1986. After incubation with [$^3$H]thymidine the cells were rinsed three times with PBS and three times with 5% trichloracetic acid (TCA). Then the cells were dissociated with 0.1 N NaOH, and after HCl neutralisation the radioactivity was measured in a liquid scintillation counter using Triton X-100-toluene-based scintillation liquid.

Total cholesterol content and DNA synthesis were determined in cell cultures (eight wells for each parameter) incubated without drug. The values obtained served as the control ones. The results were expressed as per cent of control for each atherosclerotic cellular parameter.

For confirmation of antiatherosclerotic activity, further independent experiments on cell cultures obtained from two other cell isolations were performed. Thus, the final conclusion was based on the results of at least three independent experiments.

Antiatheroaenic Effects

Atherogenesis in primary smooth muscle cells derived from grossly uninvolved human aortic intima was imitated by adding atherogenic blood serum of patients with angiographically assessed coronary atherosclerosis. Earlier it had been found that such serum causes atherosclerotic manifestations at the cellular level, namely: induction of lipid accumulation in cultured cells, stimulation of cell proliferation and extracellular matrix synthesis [Orekhov et al., 1990b, Triggerlike stimulation of cholesterol accumulation and DNA and extracellular matrix synthesis induced by atherogenic serum or low density lipoprotein in cultured cells. Circ. Res. 66: 311–320]. Atherogenic serum capable of inducing significant increase in total cholesterol levels of cultured cells within 24-hour incubation was prepared from blood taken from normolipidemic, non-diabetic men with angiographically assessed coronary atherosclerosis. Atherogenic blood serum was prepared from pooled blood of 10–15 patients and tested for atherogenicity as described [Chazov et al., 1986, Atherogenicity of blood serum from patients with coronary heart disease, Lancet 2: 595–598, Orekhov et al., 1988, Blood serum atherogenicity associated with coronary atherosclerosis. Evidence for nonlipid factor providing atherogenicity of low-density lipoproteins and an approach to its elimination. Circ. Res. 62: 421–4291]. Detailed characteristics of atherogenic serum are described elsewhere [Chazov et al., 1986]. Only sera causing statistically significant elevation of total intracellular cholesterol in cultured normal aortic cells within 24 hours were used.

Forty microliters of atherogenic serum were added to each well of 96-well tissue culture plates containing 60 µl growth medium. Ten microliters of dissolved moxonidine were added to nine wells of a seven-day cell culture simultaneously with atherogenic serum. At the same time, 10 µl of Medium 199 containing 1 µCi/ml [$^3$H]thymidine was added to three of six wells. To three other wells 10 µl Medium 199 containing 1 µCi/ml [$^{14}$C]leucine was added. The remaining three wells were supplemented with 10 µl Medium 199. After a 24-hour incubation (on the eighth day in culture) total intracellular cholesterol content as well as DNA synthesis were determined as described above.

Cell parameters were determined in cell cultures (eight wells for each parameter) incubated without drug and patients' serum (standard conditions). Obtained values served as the standard ones. All the examined parameters were determined in cells incubated during 24 hours with atherogenic serum but without moxonidine. The results were expressed as per cent of increment over standard value for each atherosclerotic cell parameter.

For confirmation of anti-atherogenic activity, further independent experiments on cell cultures obtained from two other cell isolations were performed. Thus, the final conclusion was based on the results of at least three independent experiments.

RESULTS

Antiatherosclerotic Effects

Antiatherosclerotic effects, i.e. effects imitating the regression of atherosclerosis in a cell culture, were examined on smooth muscle cells derived from an atherosclerotic plaque, as described above. These cells differ considerably from the normal cells cultured from uninvolved intima in their cholesterol content. The mean cholesterol content in the cells cultured from the plaque was five-fold higher than that in the cells cultured from uninvolved intima. Proliferative activity was about two-fold higher than in a primary cell culture derived from uninvolved intima.

During a 24-hour incubation with plaque cells moxonidine at $10^{-8}$–$10^{-5}$ M significantly lowered the intracellular cholesterol content by 20–30%. The concentration dependence curve for moxonidine effect on the cholesterol content of cells derived from plaque had a bell-like shape, similar to the experiments performed on a culture of normal cells.

Moxonidine also inhibited proliferative activity of cells cultured from an atherosclerotic plaque at $10^{-7}$ M.

Antiatherogenic Effects

In order to reveal antiatherogenic activity, i.e. the activity imitating the prevention of atherosclerosis at the cell level, smooth cells of uninvolved human aortic intima were used and atherogenic serum obtained from patients with coronary atherosclerosis, as described above. This serum induced a statistically significant 1.3- to 1.6-fold increase in the cholesterol content of cultured cells. Increment of the cholesterol content over the standard level was assumed as a 100% atherogenic effect.

At concentrations of $10^{-7}$–$10^{-5}$ M, moxonidine considerably decreased intracellular cholesterol accumulation induced by atherogenic serum. At concentrations $10^{-6}$–$10^{-5}$ M, the effect of moxonidine was significant.

Atherogenic serum significantly stimulated proliferative activity of intimal smooth muscle cells estimated by [$^3$H]

thymidine incorporation into cellular DNA. Thymidine incorporation increased by 30–90% in the presence of atherogenic serum. At concentrations $10^{-8}$–$10^{-5}$ M, moxonidine inhibited stimulation of proliferative activity induced by atherogenic serum.

I claim:

1. A method of treating atherosclerosis comprising administering to a human in need of treatment for atherosclerosis an effective amount of moxonidine, or a pharmaceutically acceptable salt thereof.

2. The method of claim 1 wherein the moxonidine is administered in a dosage of from 0.01 to 2.0 mg/day.

3. The method of claim 1 wherein the moxonidine is administered in a dosage of from 0.1 to 1.0 mg/day.

4. A method of preventing atherosclerotic lesions and plaque formation comprising administering to a human in need thereof an effective amount of moxonidine, or a pharmaceutically acceptable salt thereof.

5. The method of claim 4 wherein the moxonidine is administered in a dosage of from 0.01 to 2.0 mg/day.

6. The method of claim 4 wherein the moxonidine is administered in a dosage of from 0.1 to 1.0 mg/day.

7. A method of inhibiting atherogenesis comprising administering to a human in need thereof an effective amount of moxonidine, or a pharmaceutically acceptable salt thereof.

8. The method of claim 7 wherein the moxonidine is administered in a dosage of from 0.01 to 2.0 mg/day.

9. The method of claim 7 wherein the moxonidine is administered in a dosage of from 0.1 to 1.0 mg/day.

10. A method of decreasing intracellular cholesterol accumulation comprising administering to a human in need thereof an effective amount of moxonidine, or a pharmaceutically acceptable salt thereof.

11. The method of claim 10 wherein the moxonidine is administered in a dosage of from 0.01 to 2.0 mg/day.

12. The method of claim 10 wherein the moxonidine is administered in a dosage of from 0.1 to 1.0 mg/day.

* * * * *